United States Patent
Herron et al.

(10) Patent No.: US 10,564,114 B2
(45) Date of Patent: Feb. 18, 2020

(54) METHOD FOR THE DETECTION AND/OR DIAGNOSIS OF EATING DISORDERS AND MALNUTRITION USING X-RAY DIFFRACTION

(71) Applicant: Structure-ase, Inc., Saratoga Springs, UT (US)

(72) Inventors: Steven Richard Herron, Saratoga Springs, UT (US); Kent Hatch, Saratoga Springs, UT (US); Savannah Marriott, Saratoga Springs, UT (US); Diane Spangler, Saratoga Springs, UT (US)

(73) Assignee: STRUCTURE-ASE INCORPORATED, Saratoga Springs, UT (US)

( * ) Notice: Subject to any disclaimer, the term of this patent is extended or adjusted under 35 U.S.C. 154(b) by 578 days.

(21) Appl. No.: 15/315,528

(22) PCT Filed: Jun. 3, 2015

(86) PCT No.: PCT/US2015/034062
§ 371 (c)(1),
(2) Date: Dec. 1, 2016

(87) PCT Pub. No.: WO2015/187874
PCT Pub. Date: Dec. 10, 2015

(65) Prior Publication Data
US 2017/0115240 A1    Apr. 27, 2017

Related U.S. Application Data

(60) Provisional application No. 62/009,228, filed on Jun. 7, 2014.

(51) Int. Cl.
*G01N 23/20* (2018.01)
*G01N 23/2055* (2018.01)
*G01N 33/483* (2006.01)

(52) U.S. Cl.
CPC ..... *G01N 23/2055* (2013.01); *G01N 33/4833* (2013.01); *G01N 2223/0566* (2013.01);
(Continued)

(58) Field of Classification Search
None
See application file for complete search history.

(56) References Cited

U.S. PATENT DOCUMENTS 3,660,566 A * 5/1972 Masurat ................. A61K 8/985
424/574
8,258,093 B2 * 9/2012 Van Dyke ............ A61K 38/015
514/1

(Continued)

*Primary Examiner* — Thomas R Artman

(57) ABSTRACT

Alternatives described herein relate to methods for detecting, identifying, and/or diagnosing eating disorders, nutritional deficiencies, and/or malnutrition, including conditions such as bulimia nervosa and/or anorexia nervosa, by using X-ray diffraction on a sample of a tested subject's hair. In some alternatives, once an eating disorder, nutritional deficiency, or malnutrition is detected, identified, or diagnosed using the X-ray diffraction approaches set forth herein, a subject identified as having an eating disorder, nutritional deficiency, or malnutrition is provided counseling for the disorder and/or a medicament to treat, inhibit, or ameliorate said eating disorder or malnutrition, including Prozac, ami trip tyline, fluoxe tine, imipramine, Nardil, Tofranil, desipramine, Sarafem, Norpramin, and/or phenelzine.

9 Claims, 2 Drawing Sheets

(52) U.S. Cl.
CPC .............. *G01N 2223/612* (2013.01); *G01N 2223/6126* (2013.01)

(56) References Cited

U.S. PATENT DOCUMENTS

| | | | |
|---|---|---|---|
| 8,273,702 B2* | 9/2012 | Van Dyke | A61K 38/015 514/1 |
| 8,299,013 B2* | 10/2012 | Van Dyke | A61L 15/32 514/1 |
| 2008/0274165 A1* | 11/2008 | Van Dyke | A61K 38/015 424/447 |
| 2011/0142910 A1* | 6/2011 | Van Dyke | A61L 15/32 424/445 |
| 2012/0009237 A1* | 1/2012 | Van Dyke | A61K 38/015 424/402 |
| 2017/0115240 A1* | 4/2017 | Herron | G01N 23/2055 |
| 2019/0170726 A1* | 6/2019 | Tsuji | G01N 23/223 |

* cited by examiner

METHOD FOR THE DETECTION AND/OR DIAGNOSIS OF EATING DISORDERS AND MALNUTRITION USING X-RAY DIFFRACTION

RELATED APPLICATIONS

This application is a U.S. National Phase Application of PCT International Application Number PCT/US2015/034062, filed on Jun. 3, 2015, designating the United States of America and published in the English language, which is an International Application of and claims the benefit of U.S. Provisional Patent Application No. 62/009,228, filed Jun. 7, 2014, the disclosures of which are hereby expressly incorporated by reference in their entireties.

FIELD OF THE INVENTION

Alternatives described herein relate to methods for detecting, identifying, and/or diagnosing eating disorders and/or malnutrition in a subject, including conditions such as bulimia nervosa and/or anorexia nervosa, by using X-ray diffraction on a sample of a tested subject's hair. In some embodiments, once an eating disorder and/or malnutrition is detected, identified, or diagnosed using the X-ray diffraction approaches set forth herein, a subject identified as having an eating disorder and/or malnutrition is provided counseling for the disorder and/or a medicament to treat, inhibit, and/or ameliorate said eating disorder or malnutrition.

BACKGROUND OF THE INVENTION

Approximately 1-5% of all high school and college-aged women in the United States are affected in some way by a pathological dietary practice (Harrison K., Cantor J. J. Commun. 1997, 47:40: Thomsen S. R., McCoy J. K., Williams M. Eat. Disord. 2001, 9:49). The most common pathological dietary practices are anorexia nervosa and bulimia nervosa. Anorexia nervosa is characterized by an intense fear of weight gain and extremely low body weight. This fear is driven by a distorted view of body image and leads to a denial of the pathological condition (American Psychiatric Association. Diagnostic and Statistical Manual for Mental Disorders. APA Press: Washington, D.C., 1994, 2000; Vitousek K. B., Daly J., Heiser C. Int. J. Eat. Disord. 1991, 10:647). Bulimia nervosa is characterized by recurrent cycles of binge eating and purging, through the use of self-induced vomiting, laxatives, enemas, and/or diuretics (American Psychiatric Association. Diagnostic and Statistical Manual for Mental Disorders. APA Press: Washington, D.C., 1994, 2000; Austin S. B. Psychol. Med. 2000, 30:1249; Fairburn S. G., Harrison P. J. Lancet 2003, 361:407). A small percentage, approximately 6-8%, of bulimia nervosa patients are non-purging and use excessive exercise and/or fasting after a binge to offset the caloric intake. While individuals with anorexia nervosa have a low body weight, individuals with bulimia nervosa can be of any body type making clinical detection more difficult.

The detection and treatment of anorexia nervosa and bulimia nervosa have been hampered by the lack of reliable clinical tests for these disease states. Currently, the diagnosis of anorexia nervosa and bulimia nervosa is based upon self-reporting, questionnaires, and some severe health indicators. The psychological questions are more highly weighted, because the physiological indicators are more subjective. This is especially true of pre and early adolescent individuals, where physiological indicators, body mass index values and menstrual cycles, are not routine. Standard questionnaires and interviews designed to assess anorexia nervosa and bulimia nervosa rely on accurate self-reporting by the patient. Common to both anorexia nervosa and bulimia nervosa, is an element of denial. Since diagnosis is based upon self-reporting and questionnaires, an affected individual usually does not come to the attention of a medical practitioner until a serious associated medical condition or psychological problem appears. Early detection of anorexia nervosa and bulimia nervosa would help doctors identify eating disorder sufferers before the associated nutritional deficiencies can cause severe health problems.

When X-rays come in contact with matter, the resulting scattering and change of intensity of the rays can yield significant structural information about the composition of the sample. In fiber X-ray diffraction, the diffraction pattern consists of a series of intensity rings perpendicular to the fiber axis. Biological fibers contain elongated molecules along the axis of the fiber that are aligned parallel to each other. Small Angle X-ray Scattering (SAXS) diffraction has been used to examine the filament structure of human hairs as far back as 1995 (Wilk K. E., James Amemiya Y. Biochimica et Biophysica Acta 1995, 1245:392) Hair samples from individuals who have been exposed to mercury exhibit altered SAXS diffraction patterns. While mercury does not interfere with the intermediate filaments of hair, it does disrupt the proteoglycan layer in the extra cellular matrix of hair, affecting SAXS patterns (Xing X., Du R., Li Y., Li B., Cai Q., Mo G., Gong Y., Chen Z., Wu Z. Environ Sci Technol 2013, 47:11214). Although significant changes to the hair structure can be detected by X-ray diffraction, a recent study reported that the X-ray diffraction patterns of hair from healthy individuals are highly consistent (Yang F. C., Zhang Y., Rheinstadter M. C. Peer J 2014, 2:e619).

Hair follicle cells have a high metabolic activity. As a result, hair growth and development can be affected by dietary or micronutrient deficiencies. Previous work has shown that deficiencies in vitamin A, vitamin B12, biotin, vitamin C, zinc, selenium, and essential fatty acids can alter the hair's growth rate, pigmentation, and structure (Goldberg L. J., Lenzy Y. Clinics in Dermatology 2010, 28:412; Ginner A. M. Dermatol Clin 2013, 31:167). In diagnosing these deficiencies, typically the hair is examined for such characteristics as hair diameter, hair pigmentation, decreased hair quality, increased fragility, brittleness, or the ease with which it can be pulled from the scalp, However, these diagnostic signals are highly subjective because of a lack of laboratory standards or clear correlations between nutritional status and the previously stated characteristics (Ginner A. M. Dermatol Clin 2013, 31:167).

SUMMARY OF THE INVENTION

It has been discovered that X-ray diffraction of a subject's hair can be used to identify and/or diagnose the presence of malnutrition and/or an eating disorder, such as anorexia nervosa and/or bulimia nervosa, in said subject. Accordingly, many of the alternatives described herein concern the identification or diagnosis of malnutrition and/or an eating disorder, such as anorexia nervosa and/or bulimia nervosa, in a subject, such as a human or animal (e.g., domestic or farm animals) by analyzing a hair sample from said subject using X-ray diffraction. In some alternatives, the X-ray diffraction pattern of a hair sample from a tested subject is compared to the X-ray diffraction pattern of a hair sample from a control subject, wherein said control subject is a healthy individual. In some alternatives, the X-ray diffraction pattern of a hair sample from a tested subject is compared to the X-ray diffraction pattern of a hair sample from a control subject, wherein said control subject is an individual that is malnourished, has a nutritional deficiency, or suffers from an eating disorder, such as anorexia nervosa and/or bulimia nervosa. In some alternatives, the X-ray diffraction pattern of a hair sample from a tested subject is compared to the X-ray diffraction pattern of a hair sample from control subjects, wherein at least one control subject is a healthy individual and/or at least one control subject is an individual that is malnourished, has a nutritional deficiency, or suffers from an eating disorder, such as anorexia nervosa and/or bulimia nervosa. In some alternatives, the X-ray diffraction pattern of hair sample from the tested subject is compared to X-ray diffraction pattern of the hair sample from one or more control subjects, as set forth above, and it is determined whether said tested subject is a healthy individual or said subject is an individual that is malnourished, has a nutritional deficiency, or suffers from an eating disorder, such as anorexia nervosa and/or bulimia nervosa. In some alternatives, the X-ray diffraction pattern of the hair from the tested subject is analyzed for the presence of a pronounced ring at 40-50 Angstroms or at about 40-50 Angstroms, which is not present in an X-ray diffraction pattern of a hair sample from a healthy subject, Optionally, once a subject is identified and/or diagnosed as being malnourished, having a nutritional deficiency, or suffering from an eating disorder, such as anorexia nervosa and/or bulimia nervosa, said subject is provided counseling for the eating disorder or malnourishment and/or a medicament to treat, inhibit, or ameliorate said eating disorder or malnutrition, such as, e.g., Prozac, amitriptyline, fluoxetine, imipramine, Nardil, Tofranil, desipramine, Sarafem, Norpramin, and/or phenelzine.

In some alternatives described herein, a hair sample is taken from a subject e.g., adjacent to the skin from an individual. The subject may be a human or an animal (e.g., a dog, cat, horse, pig, goat, or bovine). The hair sample is then mounted and centered, with respect to the X-ray beam, onto the X-ray diffraction instrument. In some alternatives, the hair sample is exposed to X-rays, between 0.05 and 0.25 nM, for a period of 5 seconds to 90 minutes. That is, in some alternatives, the hair sample is exposed to X-rays at wavelengths of 0.05, 0.1, 0.15, 0.2, or 0.25 nM or a wavelength that is within a range defined by any two of the aforementioned values, for 5, 10, 20, 30, 40, or 50 seconds or 1, 2, 5, 7, 10, 20, 30, 40, 50, 60, 70, 80, or 90 minutes or for a time that is within a range defined by any two of the aforementioned times. The diffracted rays are collected on a detector, while the primary beam is blocked by the beam stop. The diffraction rings are then analyzed to determine whether the individual is suffering from an eating disorder, nutritional deficiency, or from malnutrition. As set forth above, in some alternatives, the X-ray diffraction pattern of a hair sample from a tested subject is compared to the X-ray diffraction pattern of a hair sample from a control subject, wherein said control subject is a healthy individual; in some alternatives, the X-ray diffraction pattern of a hair sample from a tested subject is compared to the X-ray diffraction pattern of a hair sample from a control subject, wherein said control subject is an individual that is malnourished, has a nutritional deficiency, or suffers from an eating disorder, such as anorexia nervosa and/or bulimia nervosa; and in some alternatives, the X-ray diffraction pattern of a hair sample from a tested subject is compared to the X-ray diffraction pattern of a hair sample from control subjects, wherein at least one control subject is a healthy individual and/or at least one control subject is an individual that is malnourished, has a nutritional deficiency or suffers from an eating disorder, such as anorexia nervosa and/or bulimia nervosa. In some alternatives, the X-ray diffraction pattern of the hair sample from the tested subject is compared to X-ray diffraction pattern of the hair sample from one or more control subjects, as set forth above, and it is determined whether said tested subject is a healthy individual or said subject is an individual that is malnourished, has a nutritional deficiency, or suffers from an eating disorder, such as anorexia nervosa and/or bulimia nervosa. In some alternatives, the X-ray diffraction pattern of the hair from the tested subject is analyzed for the presence of a pronounced ring at 40-50 Angstroms or at about 40-50 Angstroms, which is not present in an X-ray diffraction pattern of a hair sample from a healthy individual. Optionally, once a subject is identified and/or diagnosed as being malnourished, having a nutritional deficiency, or suffering from an eating disorder, such as anorexia nervosa and/or bulimia nervosa, said subject is provided counseling for the eating disorder, nutritional deficiency, or malnourishment and/or a medicament to treat, inhibit, or ameliorate said eating disorder or malnutrition, such as, e.g., Prozac, amitriptyline, fluoxetine, imipramine, Nardil, Tofranil, desipramine, Sarafem, Norpramin, and/or phenelzine, Accordingly, desirable alternatives include:

1. A method for detecting or identifying the presence of an eating disorder and/or malnutrition in a subject, such as a human or an animal, comprising:
   obtaining a hair sample from a subject, e.g., a subject suspected of having an eating disorder and/or malnutrition; exposing the hair sample to X-ray diffraction analysis so as to produce an X-ray diffraction pattern; and
   detecting a change or difference in the X-ray diffraction pattern of the hair from the subject with respect to a control X-ray diffraction pattern, obtained from the analysis of a hair sample from a healthy subject,
   wherein the detected change or difference in the X-ray diffraction pattern of the hair from the subject with respect to a control X-ray diffraction pattern is indicative of the presence of an eating disorder and/or malnutrition in the subject. Optionally, once the subject is detected or identified as having an eating disorder and/or malnutrition, said subject is provided counseling and/or a medicament to treat, inhibit, or ameliorate said eating disorder or malnutrition, such as, e.g., Prozac, amitriptyline, fluoxetine, imipramine, Nardil, Tofranil, desipramine, Sarafem, Norpramin, and/or phenelzine.
2. The method of alternative 1, wherein the eating disorder is bulimia or anorexia.
3. The method of any one of alternatives 1-2, wherein the hair sample comprises east one hair.
4. The method of any one of alternatives 1-3, wherein the hair sample is taken from the scalp, pubic area, arm, arm pit, leg, or trunk.
5. The method of any one of alternatives 1-4, wherein the X-ray diffraction analysis comprises fiber X-ray diffraction analysis.
6. The method of any one of alternatives 1-5, wherein the change in the X-ray diffraction pattern is a result of a change in the substructure of the hair in the subject having the eating disorder or malnutrition, compared to the substructure of the hair in a healthy subject.

7. The method of any one of alternatives 1-6, wherein the X-ray diffraction analysis comprises exposing the hair sample to X-rays while undergoing a 360 degree rotation or a still image over a period of 5 seconds to 90 minutes.

8. The method of any one of alternatives 1-7, wherein the detected changes in the X-ray diffraction pattern comprise a pronounced intensity ring at 40-50 Angstroms, which is not present in the X-ray diffraction pattern of a hair sample from a healthy subject, 9. The method of any one of alternatives 1-8, wherein the X-ray diffraction pattern of the hair sample from the healthy subject does not comprise a pronounced intensity ring at 40-50 Angstroms.

10. The method of any one of alternatives 1-9, wherein the detection of a change in the X-ray diffraction pattern is performed by a qualitative analysis of the X-ray diffraction pattern, a quantitative analysis of the X-ray diffraction pattern, or by an algorithm-based analysis of the X-ray diffraction pattern.

Preferred alternatives include:

1. A method for identifying or detecting the presence of an eating disorder, malnutrition, or a nutritional deficiency in a subject, comprising:
   a. obtaining a hair sample from a subject e.g., a subject suspected of having an eating disorder, malnutrition, or a nutritional deficiency;
   b. exposing the hair sample to X-ray diffraction analysis so as to generate an X-ray diffraction pattern; and
   c. determining that the X-ray diffraction pattern produced by the hair from the subject being tested is indicative of an eating disorder, malnutrition, or a nutritional deficiency, e.g., by comparing the X-ray diffraction produced by the hair from the subject being tested to a control X-ray diffraction pattern, which may be an X-ray diffraction pattern produced from a hair from a healthy individual or from an individual having an eating disorder, malnutrition, or a nutritional deficiency, 2. The method of alternative 1, wherein the eating disorder is bulimia or anorexia.

3. The method of any one of alternatives 1 or 2, further comprising providing said subject that is identified or detected as having an eating disorder, malnutrition, or a nutritional deficiency, counseling for the malnutrition or eating disorder and/or a medicament to treat, inhibit, or ameliorate said eating disorder or malnutrition, such as, e.g., Prozac, amitriptyline, fluoxetine, imipramine, Nardil, desipramine, Sarafem, Norpramin, and/or phenelzine.

4. The method of any one of alternatives 1-3, wherein the hair sample is taken from the scalp, pubic area, arm, arm pit, leg, face trunk, or other body part.

5. The method of any one of alternatives 1-4, wherein the X-ray diffraction analysis comprises fiber X-ray diffraction analysis.

6. The method of any one of alternatives 1-5, wherein the X-ray diffraction pattern produced by the hair from the subject being tested is indicative of an eating disorder, malnutrition, or a nutritional deficiency as a result of a change in the substructure of the hair in the subject having the eating disorder or malnutrition, as compared to the hair of a healthy individual.

7. The method of any one of alternatives 1-6, wherein the X-ray diffraction analysis comprises exposing the hair sample to X-rays while undergoing a 360 degree rotation or a still image over a period from about 5 seconds to 90 minutes such as, for 5, 10, 20, 30, 40, or 50 seconds or 1, 2, 5, 7, 10, 20, 30, 40, 50, 60, 70, 80, or 90 minutes or for a time that is within a range defined by any two of the aforementioned times.

8. The method of any one of alternatives 1-7, wherein the X-ray diffraction pattern of the subject having the eating disorder, malnutrition, or a nutritional deficiency comprises a high intensity ring at 40-50 Angstroms, which is not present in an X-ray diffraction pattern of a hair sample from a healthy individual.

9. The method of any one of alternatives 1-8, wherein X-ray diffraction pattern of a hair sample from a healthy subject does not comprise a high intensity ring at 40-50 Angstroms.

10. The method of any one of alternatives 1-9, wherein X-ray diffraction pattern is analyzed by a qualitative analysis of the X-ray diffraction pattern, a quantitative analysis of the X-ray diffraction pattern, or by an algorithm-based analysis of the X-ray diffraction pattern.

11. The method of any one of alternatives 1-10, wherein the hair sample is exposed to X-rays at wavelengths of 0.05, 0.1, 0.15, 0.2, or 0.25 nM or a wavelength that is within a range defined by any two of the aforementioned values.

BRIEF DESCRIPTION OF THE DRAWINGS

In addition to the features described above, additional features and variations will be readily apparent from the following descriptions of the drawings and exemplary embodiments. It is to be understood that these drawings depict typical alternatives, and are not intended to be limiting in scope.

DETAILED DESCRIPTION OF THE PREFERRED EMBODIMENTS

Although the invention is described in various exemplary alternatives and implementations as provided herein, it should be understood that the various features, aspects, and functionality described in one or more of the individual alternatives are not limited in their applicability to the particular alternative with which they are described. Instead, they can be applied alone or in various combinations to one or more of the other alternatives, whether the alternatives are described or whether the features are presented as being a part of the described alternative. The breadth and scope of the present invention should not be limited by any exemplary alternatives described or shown herein.

The disclosure relates generally to methods for the detection and diagnosis of eating disorders, including, for example, anorexia nervosa and bulimia nervosa. The disclosure also relates to methods for the detection and diagnosis of malnutrition and/or a nutritional deficiency. The disclosure also relates to the analysis of X-ray diffraction patterns of hair samples, wherein the analysis of the diffraction patterns enables the diagnosis and/or determination of the nutritional state of a subject e.g., a human, a domestic animal, such as dog, cat, or horse, farm animals, such as cattle, pigs, goats, or sheep, or a wild animal.

In some embodiments herein, a hair sample is obtained from a subject having or suspected of having a nutritional deficiency. In some embodiments, the hair sample may be obtained from a healthy subject. The hair sample may be a hair sample from any portion of the subject, By way of example, the hair could be obtained from the scalp, the appendages, such as the arms, arm pits, or legs, from the pubic area, trunk, or any other body hair.

In some embodiments herein, the hair sample obtained from the subject is mounted and centered with respect to the X-ray beam onto the X-ray diffraction instrument. In some embodiments, the hair sample is exposed to X-rays, between 0.05 and 0.25 nM, for a period of between 5 seconds to 90 minutes. That is, in some alternatives, the hair sample is exposed to X-rays at wavelengths of 0.05, 0.1, 0.15, 0.2, or 0.25 nM or a wavelength that is within a range defined by any two of the aforementioned values, for 5, 10, 20, 30, 40, or 50 seconds or 1, 2, 5, 7, 10, 20, 30, 40, 50, 60, 70, 80, or 90 minutes or for a time that is within a range defined by any two of the aforementioned times. The primary beam is blocked by the beam stop, and the diffracted rays are collected on a detector. The diffraction rings are analyzed to determine whether the individual is suffering from an eating disorder and/or from malnutrition.

Figure 1:
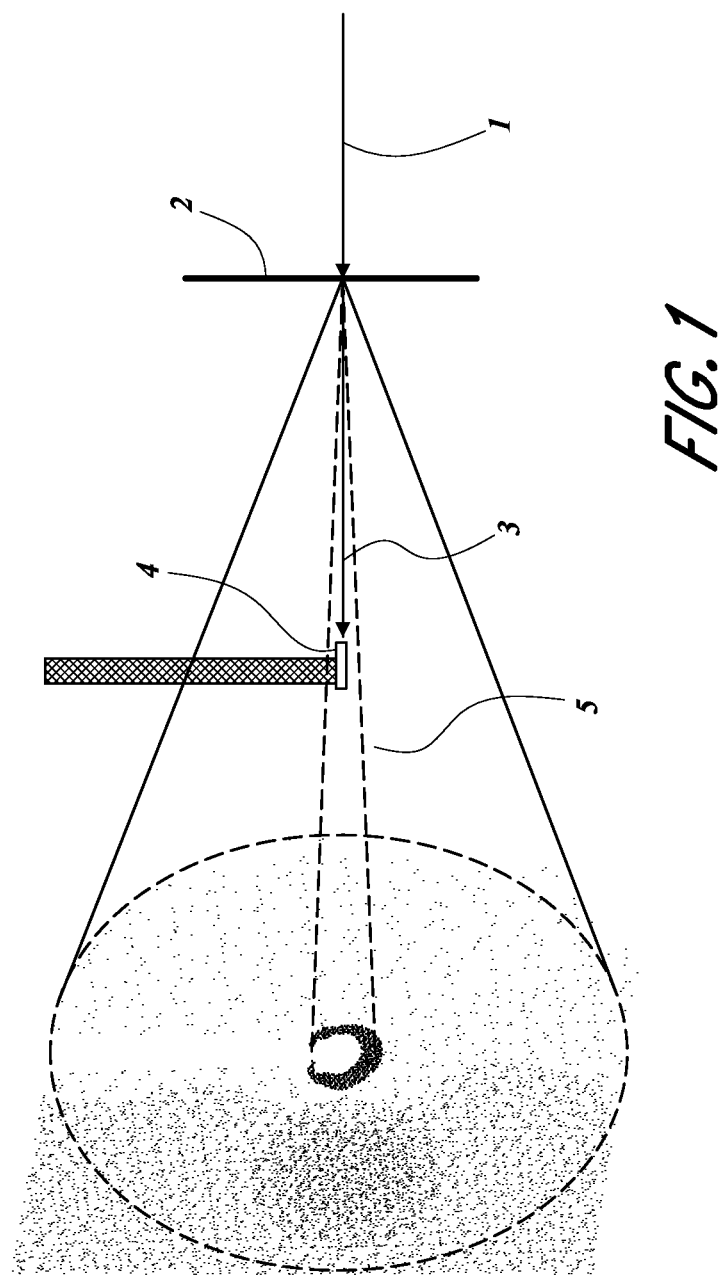
FIG. 1 shows an X-ray pattern obtained from a hair sample from a subject with an eating disorder (anorexia or bulimia) and/or suffering from malnutrition.

FIG. 1 shows one alternative of the detected diffraction rays collected on the detector. In some alternatives, the primary X-ray beam (1) irradiates a single hair (2) sample from an individual having or suspected of having a nutritional deficiency. Unscattered X-rays (3) from the primary beam are stopped by the beam stop (4). Scattered X-rays (5) from the hair sample (2) are deflected from the primary beam and strike the detector forming a primary diffraction ring at about 40-50 angstroms. In some embodiments, hair samples from individuals with an eating disorder (anorexia or bulimia) and/or suffering from malnutrition have a diffraction ring at 40-50 angstroms or about 40-50 angstroms that is absent in non-affected individuals (individuals without an eating disorder or individuals that have a healthy nutritional state).

Figure 2:
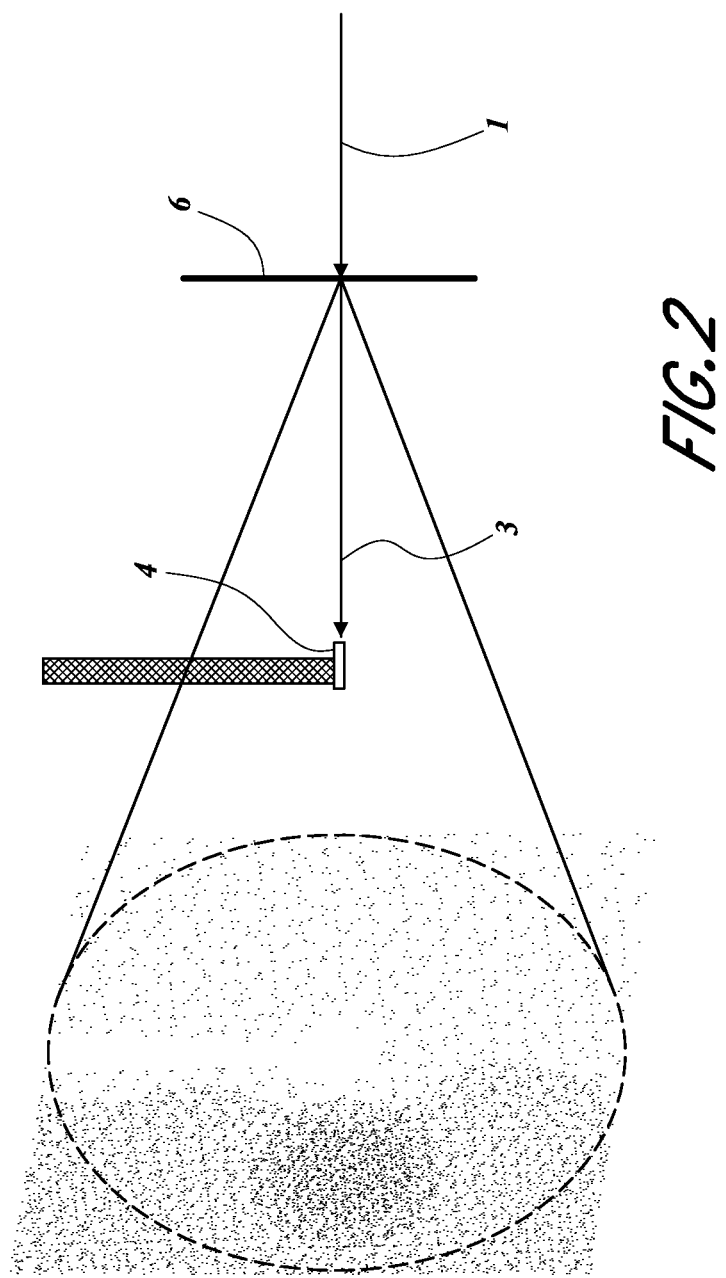
FIG. 2 shows an X-ray pattern obtained from a normal hair sample.

FIG. 2 shows one embodiment of the detected diffraction rays collected on the detector, wherein the hair sample is a hair sample from healthy individuals, or individuals having a normal feed state and who do not have a nutritional deficiency. The primary X-ray beam (1) irradiates a single hair sample (6). Unscattered X-rays (3) from the primary beam are stopped by the beam stop (4).

In some embodiments, the X-ray diffraction pattern obtained from a subject having or suspected of having a nutritional deficiency is compared to the X-ray diffraction pattern of a healthy individual. In some embodiments, a series of X-ray diffraction patterns are collected over a period of time using a new hair sample at various time points, and changes in the diffraction patterns are analyzed to determine the progression and/or onset of a nutritional deficiency. As set forth above, in some alternatives, the X-ray diffraction pattern of a hair sample from a tested subject is compared to the X-ray diffraction pattern of a hair sample from a control subject, wherein said control subject is a healthy individual; in some alternatives, the X-ray diffraction pattern of a hair sample from a tested subject is compared to the X-ray diffraction pattern of a hair sample from a control subject, wherein said control subject is an individual that is malnourished or suffers from an eating disorder, such as anorexia nervosa and/or bulimia nervosa; and in some alternatives, the X-ray diffraction pattern of a hair sample from a tested subject is compared to the X-ray diffraction pattern of a hair sample from control subjects, wherein at least one control subject is a healthy individual and at least one control subject is an individual that is malnourished or suffers from an eating disorder, such as anorexia nervosa and/or bulimia nervosa. In some alternatives, the X-ray diffraction pattern of the hair from the tested subject is analyzed for the presence of a pronounced ring at 40-50 Angstroms, or at about 40-50 Angstroms, which is not present in an X-ray diffraction pattern of a hair sample from a healthy individual. Optionally, once a subject is identified and/or diagnosed as being malnourished or suffering from an eating disorder, such as anorexia nervosa and/or bulimia nervosa, said subject is provided counseling for the malnutrition or eating disorder and/or a medicament to treat, inhibit, or ameliorate said eating disorder or malnutrition, such as, e.g., Prozac, amitriptyline, fluoxetine, imipramine, Nardil, Tofranil, desipramine, Sarafem, Norpramin, and/or phenelzine.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for identifying or detecting the presence of an eating disorder, malnutrition, or a nutritional deficiency in a subject, comprising:
   measuring an X-ray diffraction pattern of a hair sample from a subject; and
   identifying a high intensity ring in the diffraction pattern at 40-50 Angstroms;
   wherein the high intensity ring at 40-50 Angstroms is indicative of an eating disorder, malnutrition, or a nutritional deficiency in said subject.

2. The method of claim 1, wherein the eating disorder is bulimia or anorexia.

3. The method of claim 1, further comprising providing said subject having an eating disorder, malnutrition, or a nutritional deficiency, counseling for the malnutrition or eating disorder.

4. The method of claim 1, wherein the hair sample is taken from the scalp, pubic area, arm, arm pit, leg, face, trunk, or other body part of said subject.

5. The method of claim 1, wherein measuring the X-ray diffraction pattern comprises a fiber X-ray diffraction analysis.

6. The method of claim 1, wherein the X-ray diffraction pattern produced by the hair from the subject being tested is indicative of an eating disorder, malnutrition, or a nutritional deficiency as a result of a change in the substructure of the hair in the subject having the eating disorder or malnutrition, as compared to the hair of a control subject.

7. The method of claim 1, wherein measuring the X-ray diffraction pattern comprises exposing the hair sample to X-rays while undergoing a 360 degree rotation or a still image over a period from 5 seconds to 90 minutes.

8. The method of claim 1, wherein the X-ray diffraction pattern is analyzed by a qualitative analysis of the X-ray diffraction pattern, a quantitative analysis of the X-ray diffraction pattern, or by an algorithm-based analysis of the X-ray diffraction pattern.

9. The method of claim 1, wherein the hair sample is exposed to X-rays at wavelengths of 0.05, 0.1, 0.15, 0.2, or 0.25 nM.

* * * * *